(12) United States Patent
Endo et al.

(10) Patent No.: US 7,403,594 B2
(45) Date of Patent: Jul. 22, 2008

(54) RADIATION IMAGING APPARATUS AND CONTROL METHOD THEREFOR

(75) Inventors: Tadao Endo, Honjo (JP); Toshio Kameshima, Kumagaya (JP); Tomoyuki Yagi, Chofu (JP); Katsuro Takenaka, Kodama-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/094,134

(22) Filed: Mar. 31, 2005

(65) Prior Publication Data

US 2005/0220269 A1    Oct. 6, 2005

(30) Foreign Application Priority Data

Mar. 31, 2004   (JP)   .............................. 2004-106387

(51) Int. Cl.
  H05G 1/56   (2006.01)
  H05G 1/64   (2006.01)
  G01T 1/24   (2006.01)

(52) U.S. Cl. .................. 378/114; 378/98.8; 250/370.09

(58) Field of Classification Search ............... 378/98.8, 378/114–116; 250/370.09, 370.11
See application file for complete search history.

(56) References Cited

U.S. PATENT DOCUMENTS

| | | | | |
|---|---|---|---|---|
| 4,392,236 | A | * | 7/1983 | Sandstrom et al. ............. 378/45 |
| 5,483,071 | A | * | 1/1996 | Oikawa et al. ......... 250/370.09 |
| 5,629,517 | A | * | 5/1997 | Jackson et al. ........... 250/208.1 |
| 5,818,898 | A | * | 10/1998 | Tsukamoto et al. ........ 378/98.8 |
| 6,005,911 | A | * | 12/1999 | Cheung ....................... 378/37 |
| 6,630,676 | B2 | * | 10/2003 | Takemoto ............... 250/370.09 |
| 6,847,698 | B2 | * | 1/2005 | Kaifu et al. .................... 378/97 |
| 6,933,503 | B2 | * | 8/2005 | Sipila et al. ............ 250/370.09 |
| 6,952,015 | B2 | | 10/2005 | Kameshima ........... 250/370.11 |
| 6,952,464 | B2 | | 10/2005 | Endo ........................ 378/98.11 |
| 6,985,555 | B2 | | 1/2006 | Endo ........................ 378/98.11 |
| 7,002,157 | B2 | | 2/2006 | Kameshima ........... 250/370.11 |
| 7,012,260 | B2 | | 3/2006 | Endo ..................... 250/370.11 |
| 2001/0012070 | A1 | | 8/2001 | Enod et al. .................. 348/302 |
| 2002/0044141 | A1 | * | 4/2002 | Watanabe et al. ........... 345/204 |

(Continued)

FOREIGN PATENT DOCUMENTS

JP   9-307698   11/1997

(Continued)

*Primary Examiner*—Edward J. Glick
*Assistant Examiner*—Anastasia S. Midkiff
(74) *Attorney, Agent, or Firm*—Fitzpatrick, Cella, Harper & Scinto

(57) ABSTRACT

A lamp emits pulse-shaped visible light when a wait period begins. If a radiation emission switch is not pressed in the wait period, X-ray radiation is not emitted from an X-ray source, and no charges are accumulated in photoelectric conversion elements of an X-ray imaging apparatus. In a non-read period, although signals are sequentially read from the photoelectric conversion elements, an output signal does not change. When the radiation emission switch is pressed in synchronization with a radiation-induced signal in a certain wait period, the X-ray source emits X-rays. After irradiation of X-rays, a photoelectric conversion period transitions to an actual read period. In the photoelectric conversion period, X-rays are emitted and transmitted X-ray information of a patient are accumulated in the photoelectric conversion elements of the X-ray imaging apparatus. In the actual read period, the accumulated information is read.

22 Claims, 10 Drawing Sheets

U.S. PATENT DOCUMENTS

| | | | |
|---|---|---|---|
| 2004/0114725 A1* | 6/2004 | Yamamoto | 378/189 |
| 2005/0082491 A1* | 4/2005 | Seppi et al. | 250/370.11 |
| 2005/0088566 A1* | 4/2005 | Tamura et al. | 348/362 |
| 2005/0109927 A1 | 5/2005 | Takenaka et al. | 250/252.1 |
| 2005/0199834 A1 | 9/2005 | Takenaka et al. | 250/580 |
| 2005/0200720 A1 | 9/2005 | Kameshima et al. | 348/220.1 |
| 2005/0207534 A1* | 9/2005 | Petrick et al. | 378/114 |
| 2005/0220270 A1 | 10/2005 | Kameshima et al. | 378/116 |
| 2006/0054834 A1 | 3/2006 | Kameshima | 250/370.11 |
| 2006/0071170 A1* | 4/2006 | Broennimann et al. | 250/370.09 |
| 2006/0113484 A1 | 6/2006 | Endo | 250/370.11 |

FOREIGN PATENT DOCUMENTS

JP    2002335446 A  * 11/2002

* cited by examiner

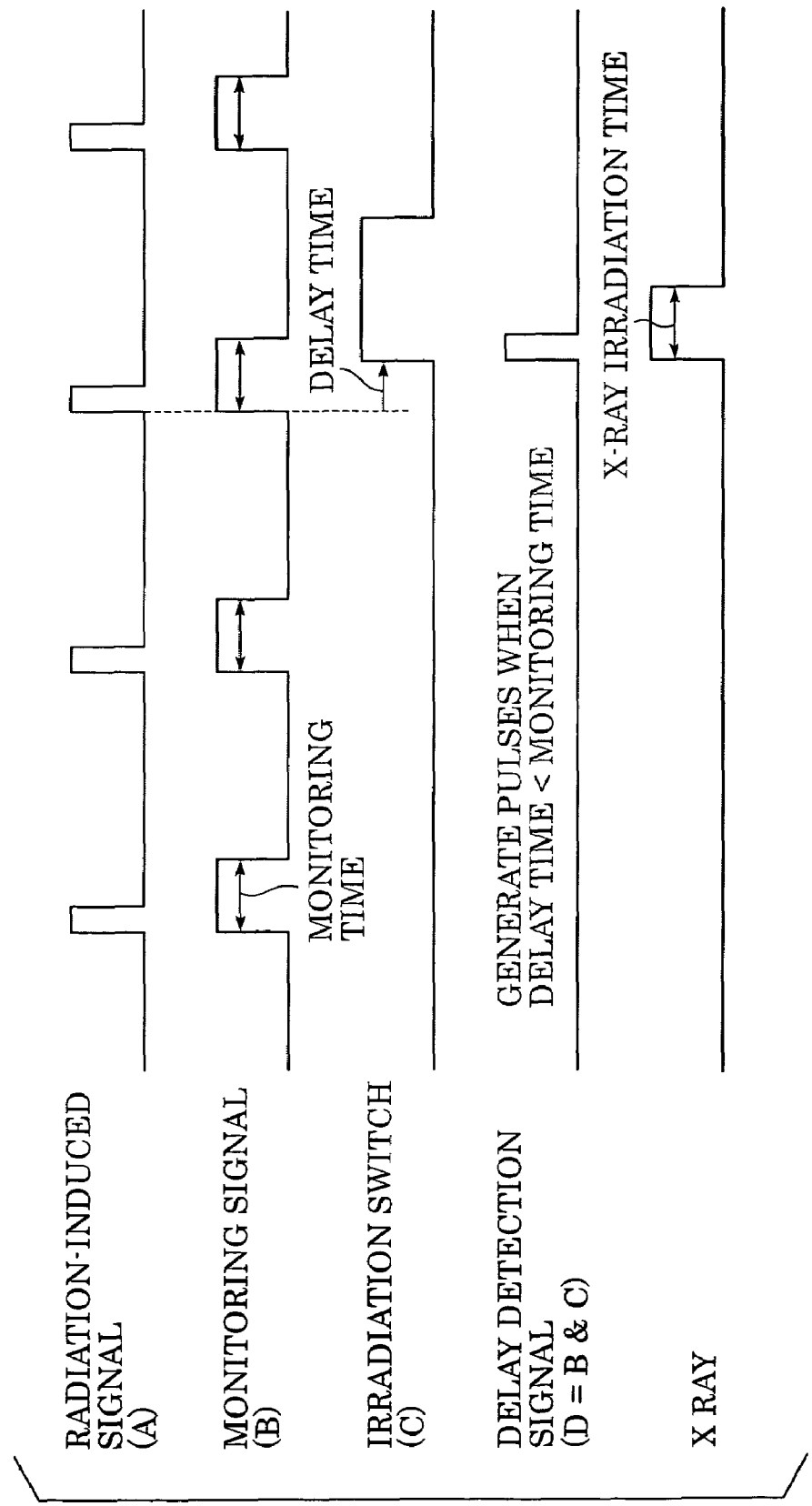

RADIATION IMAGING APPARATUS AND CONTROL METHOD THEREFOR

BACKGROUND OF THE INVENTION

1. Field of the Invention

The present invention relates to a radiation imaging apparatus suitable for a variety of applications, such as medical diagnosis and industrial non-destructive inspection, and to a control method for the radiation imaging apparatus. In the present invention, radiation includes electromagnetic radiation, such as X-ray and γ-ray, α-ray, and β-ray.

2. Description of the Related Art

Generally, X-ray radiography systems used in hospitals are of a film radiography type and an image processing type. In a film radiography type system, a patient is irradiated with X-rays and a film is exposed to the X-rays transmitted through the patient. In an image processing type system, the X-rays transmitted through the patient are converted into electrical signals for digital image processing.

One X-ray radiography system of the image processing type is a radiation imaging apparatus including a phosphor for transforming X-rays into visible light and a photoelectric conversion device for converting the visible light into electrical signals. The phosphor is exposed to X-rays transmitted through a patient to transform body information of the patient into visible light, and the transformed body information of the patient is output as electrical signals from the photoelectric conversion device. The electrical signals can further be converted into digital signals by an analog-to-digital (A/D) converter so that X-ray image information used for in recording, displaying, printing, diagnosis, etc., can be processed as digital data.

Recently, radiation imaging apparatuses including an amorphous silicon semiconductor thin-film photoelectric conversion device have been commercially available, as disclosed in Japanese Patent Laid-Open No. 9-307698.

FIG. 8 is a two-dimensional circuit diagram of a photoelectric conversion substrate of the related art including photoelectric conversion elements and switching elements made of amorphous silicon semiconductor thin films. For simplification of illustration, 3×3 pixels, i.e., nine pixels, are shown in FIG. 8.

In FIG. 8, a photoelectric conversion circuit unit (or a radiation detection circuit unit) 701 includes photoelectric conversion elements S1-1 to S3-3, switching elements (or thin-film transistors (TFTs)) T1-1 to T3-3, gate lines G1 to G3 for turning on or off the switching elements (TFTs) T1-1 to T3-3, signal lines M1 to M3, and a Vs line for applying an accumulation bias to the photoelectric conversion elements S1-1 to S3-3. The Vs line is biased by a power supply Vs. A shift register SR1 applies driving pulse voltages to the gate lines G1 to G3. A voltage Vg(on) for turning on the switching elements (TFTs) T1-1 to T3-3 and a voltage Vg(off) for turning off the switching elements (TFTs) T1-1 to T3-3 are supplied to the shift register SR1 from the outside.

A reading circuit unit 702 amplifies and serial converts parallel signals output from the signal lines M1 to M3 in the photoelectric conversion circuit unit 701, and outputs the resulting signals. The reading circuit unit 702 includes switches RES1 to RES3 for resetting the signal lines M1 to M3, amplifiers A1 to A3 for amplifying the signals on the signal lines M1 to M3, sample-hold capacitors CL1 to CL3 for temporarily storing the signals amplified by the amplifiers A1 to A3, switches Sn1 to Sn3 for performing sample hold, buffer amplifiers B1 to B3, switches Sr1 to Sr3 for converting parallel signals into serial signals, a shift register SR2 for supplying pulses for serial conversion to the switches Sr1 to Sr3, and a buffer amplifier Ab for outputting the converted serial signals.

FIG. 9 is a timing chart showing the operation of the photoelectric conversion device shown in FIG. 8.

In a photoelectric conversion period, all photoelectric conversion elements S1-1 to S3-3 are in a biased state to the electric potential of the power supply Vs and are irradiated with X-rays. The photoelectric conversion elements S1-1 to S3-3 generate charges (electrons and holes) proportional to the X-ray dose. At this time, the switching elements (TFTs) T1-1 to T3-3 are still in the off position, and the generated charges are accumulated in inter-electrode capacitors of the photoelectric conversion elements S1-1 to S3-3.

In a read period, a reading operation is performed in the order of the photoelectric conversion elements S1-1 to S1-3 in the first row, the photoelectric conversion elements S2-1 to S2-3 in the second row, and the photoelectric conversion elements S3-1 to S3-3 in the third row. First, the shift register SR1 supplies gate pulses to the gate line G1 associated with the switching elements (TFTs) T1-1 to T1-3 in the first row to perform the reading operation of the photoelectric conversion elements S1-1 to S1-3. The high level of the gate pulse corresponds to the voltage Vg(on) supplied from the outside. The switching elements (TFTs) T1-1 to T1-3 are then turned on, and the signal charges accumulated in the photoelectric conversion elements S1-1 to S1-3 are transferred to the signal lines M1 to M3. The signal charges transferred to the signal lines M1 to M3 are amplified by the amplifiers A1 to A3. Although not shown in FIG. 8, reading capacitors are added to the signal lines M1 to M3, and the signal charges are transferred to the reading capacitors via the switching elements (TFTs) T1-1 to T1-3. For example, the reading capacitor added to the signal line M1 corresponds to the sum of inter-electrode capacitors (Cgs) between gates and sources of the switching elements (TFTs) T1-1 to T3-1 connected to the signal line M, i.e., three capacitors.

An SMPL signal is turned on to transfer the signal charges to the sample-hold capacitors CL1 to CL3, and the SMPL signal is off to hold them. When pulses are applied from the shift register SR2 to the switches Sr1, Sr2, and Sr3 in this order, the signals held in the sample-hold capacitors CL1 to CL3 are output as an output signal Vout from the amplifier Ab in the order of the sample-hold capacitors CL1, CL2, and CL3 to an A/D conversion circuit unit. Thus, the photoelectric converted signals of the photoelectric conversion elements S1-1, S1-2, and S1-3 in the first row are sequentially output.

After the signal lines M1 to M3 are reset to a ground (GND) potential, the shift register SR1 supplies gate pulses to the gate line G2 associated with the switching elements (TFTs) T2-1 to T2-3 in the second row to perform the reading operation of the photoelectric conversion elements S1-1 to S1-3. The reading operation of the photoelectric conversion elements S2-1 to S2-3 in the second row and the reading operation of the photoelectric conversion elements S3-1 to S3-3 in the third row are sequentially performed. The sample hold of the signals on the signal lines M1 to M3 into the sample-hold capacitors CL1 to CL3 allows the signal charges of the photoelectric conversion elements S2-1 to S2-3 in the second row and the photoelectric conversion elements S3-1 to S3-3 in the third row to be transferred using the shift register SR1 while serially converting the signals for the first and second rows using the shift register SR2. Specifically, the signals on the signal lines M1 to M3 are sampled and held in the sample-hold capacitors CL1 to CL3 by the SMPL signal for the first row, and the signal lines M1 to M3 are reset to the GND potential by a cres signal (RC1). Then, gate pulses are applied to the gate line G2. Thus, while the shift register SR2 performs serial conversion on the signals for the first row, the shift register SR1 transfers the signal charges of the photoelectric conversion elements S2-1 to S2-3 in the second row.

Therefore, the signal charges of all photoelectric conversion elements from the first row to the third row can be output to obtain a single still image. The photoelectric conversion period and the read period, in which an image is obtained, are referred to a reading operation period.

In an X-ray imaging apparatus of the related art, generally, photoelectric conversion elements made of amorphous semiconductor as a main material, such as amorphous silicon or amorphous selenium, do not provide a stable photoelectric conversion in proportion to the X-ray dose due to dark current variations immediately after applying a bias.

Therefore, although not shown in FIG. 9, the X-ray imaging apparatus of the related art has an idling operation period of at least several seconds prior to the photoelectric conversion period. The idling operation period alternately includes a wait period and a read period. In the wait period, X-rays are not emitted or charges are not read. The idling operation period provides a stable dark characteristic in the photoelectric conversion period during which X-rays are emitted.

In the X-ray imaging apparatus, a radiographer, such as an X-ray engineer, presses an X-ray emission switch (or irradiation switch) to emit X-rays. However, the idling operation period makes it difficult to synchronize a reading operation of the X-ray imaging apparatus with X-ray emission. For example, if the irradiation switch is pressed in the read period of the idling operation period, X-rays enter the photoelectric conversion circuit unit 701 while reading signal charges.

In a control method for avoiding this problem, when a radiographer, such as an X-ray engineer, presses the irradiation switch, a reading operation ends in the idling operation period, and, after the confirmation, the idling operation period transitions to the photoelectric conversion period in which X-rays are emitted.

However, this control method causes a delay between pressing the irradiation switch and emitting X-rays. A slight delay may be negligible. However, medical X-ray imaging apparatuses for use in simple thoracic radiography generally have a wide radiographic range and a large number of pixels, and therefore require approximately 0.1 to 1 seconds for reading. X-ray radiography using such medical X-ray imaging apparatuses can make radiographers uncomfortable. Another problem is that a desired image cannot be obtained due to a delay although a radiographer presses the irradiation switch at a desired time. Therefore, the chance of taking the best radiographs may be lost.

Moreover, it is necessary to electrically connect the X-ray imaging apparatus and an X-ray generator via a connection cable or the like to synchronize X-ray emission with a reading operation of the X-ray imaging apparatus after the irradiation switch is pressed by a radiographer. The connection cable is inconvenient for the radiographer particularly in radiography using a portable X-ray imaging apparatus, such as a film cassette type apparatus, and reduces the radiographic efficiency. An X-ray imaging apparatus having a connection cable can break down due to the cable being tripped over or walked on, and the radiographic operation is interrupted until the broken apparatus is repaired.

SUMMARY OF THE INVENTION

The present invention provides a radiation imaging apparatus capable of stably performing radiography while preventing a delay of radiation emission, and a control method for the radiation imaging apparatus.

In order to overcome the foregoing problems, in one aspect of the present invention, a radiation imaging apparatus includes a conversion circuit unit in which a plurality of pixels including conversion elements are arranged into an array on a substrate, a reading circuit unit that reads signals from the conversion circuit unit. A radiographic operation period in which a radiation image is taken includes an idling operation period prior to emission of radiation and a reading operation period subsequent to emission of radiation, and a radiation-induced signal is indicated to a radiographer during the idling operation period so that the radiographer can operate a radiation emission switch for instructing a radiation generator to emit radiation at a desired time subsequent to the idling operation period.

In another aspect of the present invention, a radiation imaging apparatus includes a conversion circuit unit in which a plurality of pixels including conversion elements are arranged into an array on a substrate, a reading circuit unit that reads signals from the conversion circuit unit, and a radiation emission switch for instructing a radiation generator to emit radiation. The apparatus also includes a radiation-induced signal generating unit that generates a radiation-induced signal for inducing the radiographer to operate the radiation emission switch, where the generation of the radiation-induced signal performed by the radiation-induced signal generating unit and reading of the signals from the conversion circuit unit performed by the reading circuit unit are repeated.

In another aspect of the present invention, a radiation imaging system includes a radiation generator, a conversion circuit unit in which a plurality of pixels including conversion elements are arranged into an array on a substrate, a reading circuit unit that reads signals from the conversion circuit unit, and a radiation emission switch for instructing the radiation generator to emit radiation. A radiation image is taken in a radiographic operation period that includes an idling operation period prior to emission of radiation and a reading operation period subsequent to emission of radiation. A radiation-induced signal is indicated to a radiographer during the idling operation period so that the radiographer can operate the radiation emission switch at a desired time subsequent to the idling operation period, and the radiation generator emits radiation when the radiation emission switch is operated.

In another aspect of the present invention, a radiation imaging system includes a radiation generator, a conversion circuit unit in which a plurality of pixels including conversion elements are arranged into an array on a substrate, a reading circuit unit that reads signals from the conversion circuit unit, a radiation emission switch for instructing the radiation generator to emit radiation, and a radiation-induced signal generating unit that generates a radiation-induced signal for inducing the radiographer to operate the radiation emission switch. The generation of the radiation-induced signal performed by the radiation-induced signal generating unit and reading of the signals from the conversion circuit unit performed by the reading circuit unit are repeated, and the radiation generator emits radiation when the radiation emission switch is operated.

In another aspect of the present invention, a method for controlling a radiation imaging apparatus including a conversion circuit unit in which a plurality of pixels including conversion elements are arranged into an array on a substrate, a reading circuit unit that reads signals from the conversion circuit unit, and a radiation emission switch for instructing a radiation generator to emit radiation includes performing an idling operation prior to emission of radiation, producing a radiation-induced signal perceivable by a radiographer during the idling operation. The method causes the reading circuit unit to read signals accumulated in the conversion circuit unit after the radiation emission switch is operated.

In another aspect of the present invention, a method for controlling a radiation imaging apparatus including a conversion circuit unit in which a plurality of pixels including conversion elements are arranged into an array on a substrate, a reading circuit unit that reads signals from the conversion circuit unit, a radiation emission switch for instructing a radiation generator to emit radiation, and a radiation-induced signal generating unit that generates a radiation-induced signal for inducing the radiographer to operate the radiation emission switch includes causing the radiation-induced signal generating unit to repeatedly generate the radiation-induced signal. The method also causes the reading circuit unit to repeatedly read the signals from the conversion circuit unit.

In another aspect of the present invention, a storage medium storing a program causing a computer to control a radiation imaging apparatus including a conversion circuit unit in which a plurality of pixels including conversion elements are arranged into an array on a substrate, a reading circuit unit that reads signals from the conversion circuit unit, and a radiation emission switch for instructing a radiation generator to emit radiation includes code for causing the radiation imaging apparatus to perform an idling operation prior to emission of radiation and to generate a radiation-induced signal perceivable by a radiographer during the idling operation, and code for causing the reading circuit unit to read signals accumulated in the conversion circuit unit after the radiation emission switch is operated.

In another aspect of the present invention, a storage medium storing a program causing a computer to control a radiation imaging apparatus including a conversion circuit unit in which a plurality of pixels including conversion elements are arranged into an array on a substrate, a reading circuit unit that reads signals from the conversion circuit unit, a radiation emission switch for instructing a radiation generator to emit radiation, and a radiation-induced signal generating unit that generates a radiation-induced signal for inducing the radiographer to operate the radiation emission switch includes code for causing the radiation-induced signal generating unit to repeatedly generate the radiation-induced signal, and code for causing the reading circuit unit to repeatedly read the signals from the conversion circuit unit.

According to the present invention, stable photoelectric converted signals having small dark current variations in proportional to the dose of applied radiation can be obtained. The irradiation switch is operated in synchronization with a radiation-induced signal, thus allowing radiography with small radiation delay at desired timing. Moreover, a radiographer can operate the irradiation switch while perceiving the radiation-induced signal, and therefore no electrical connection via a cable between the radiation imaging apparatus and the radiation generator is required. Thus, a portable radiation imaging apparatus, such as a film cassette type apparatus, can be realized, which is easy-to-use and safe even in emergency medical environments in which a patient is radiographed while moving the radiation generator.

Further features and advantages of the present invention will become apparent from the following description of exemplary embodiments with reference to the attached drawings.

BRIEF DESCRIPTION OF THE DRAWINGS

FIG. 10 is a timing chart showing an operation for preventing emission of X-rays.

DESCRIPTION OF THE EMBODIMENTS

Embodiments of the present invention will now be described with reference to the drawings.

First Embodiment

Figure 1:
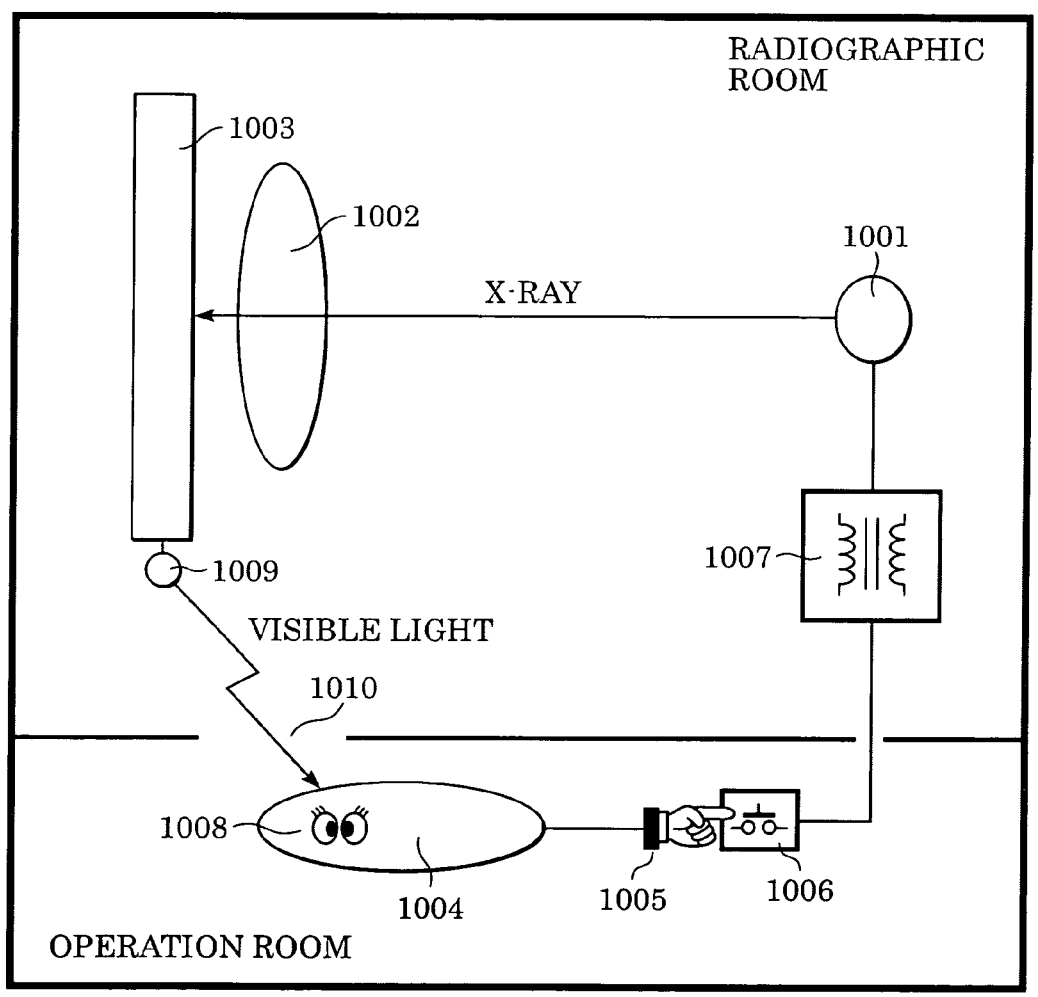
FIG. 1 is a diagram of an X-ray imaging system (radiation imaging system) according to a first embodiment of the present invention.

FIG. 1 is a diagram of an X-ray imaging system (radiation imaging system) according to a first embodiment of the present invention.

An X-ray source 1001 generates X-rays by allowing thermo-electrons emitted from a cathode filament disposed in a vacuum tube (not shown) to accelerate and strike an anode target. The target is made of, for example, tungsten or copper. A high-voltage power supply 1007 is a power supply for accelerating the thermo-electrons. When an irradiation switch 1006 is turned on, X-rays are produced from the X-ray source 1001. The irradiation switch 1006 is operated by, for example, a radiographer's hand 1005. An electron accelerating voltage (tube voltage) and a cathode filament current (or tube current) (not shown) are set in advance by a radiographer 1004 operating an operation panel (not shown).

In a radiographic room, the X-rays emitted from the X-ray source 1001 are applied to a patient 1002, and an X-ray imaging apparatus 1003 is exposed to the X-rays transmitted through the patient 1002 to create an X-ray image. The X-ray imaging apparatus 1003 has a similar structure to that shown in, for example, FIG. 8. The radiographer 1004 is in an operation room to avoid exposure to X-rays. A shield made of an X-ray absorbing material, such as lead, between the radiographic room and the operation room includes a lead-containing transparent glass window 1010 for observing the inside of the radiographic room.

The X-ray imaging apparatus 1003 includes a lamp 1009 serving as a radiation-induced signal generator for generating a radiation-induced signal. The lamp 1009 may be of any type capable of pulsing visible light, e.g., an electric lamp or a light-emitting diode (LED) lamp. The radiation imaging system according to the first embodiment includes the X-ray imaging apparatus 1003 and the lamp 1009.

Figure 2:
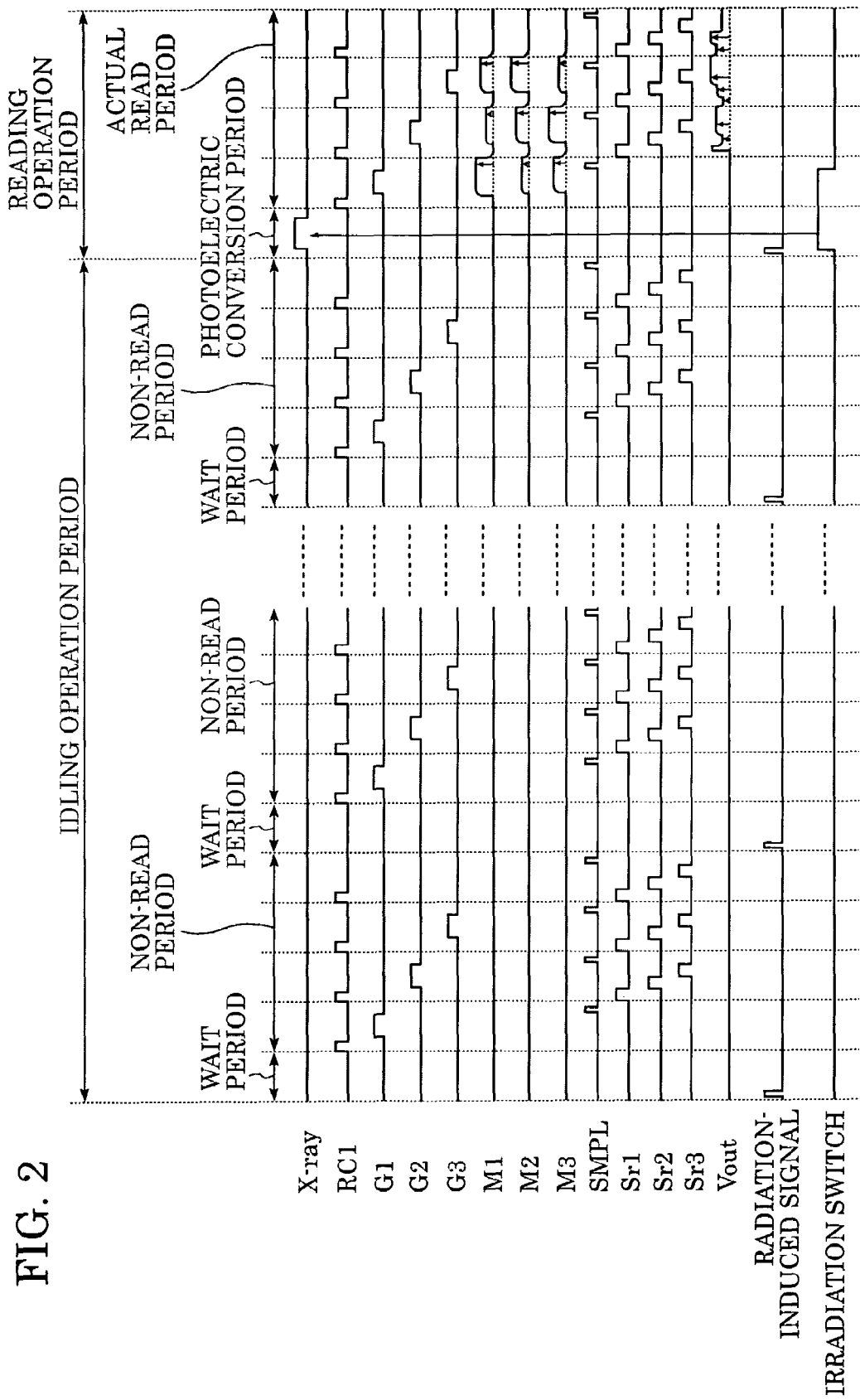
FIG. 2 is a timing chart showing the operation of the X-ray imaging system according to the first embodiment of the present invention.

FIG. 2 is a timing chart showing the operation of the X-ray imaging system according to the first embodiment of the present invention. It is assumed that the X-ray imaging apparatus 1003 has a similar structure to that shown in FIG. 8.

In the first embodiment, an idling operation period resides prior to a reading operation period. The idling operation period alternately includes wait periods and non-read periods. The wait periods and the non-read periods are repeated in the idling operation period.

When a wait period begins, the lamp 1009 emits a pulsed radiation-induced signal, e.g., visible light. Unless the irradiation switch 1006 is pressed during the wait period, X-rays are not emitted from the X-ray source 1001, and no charge is accumulated in photoelectric conversion elements of the X-ray imaging apparatus 1003.

Figure 8:
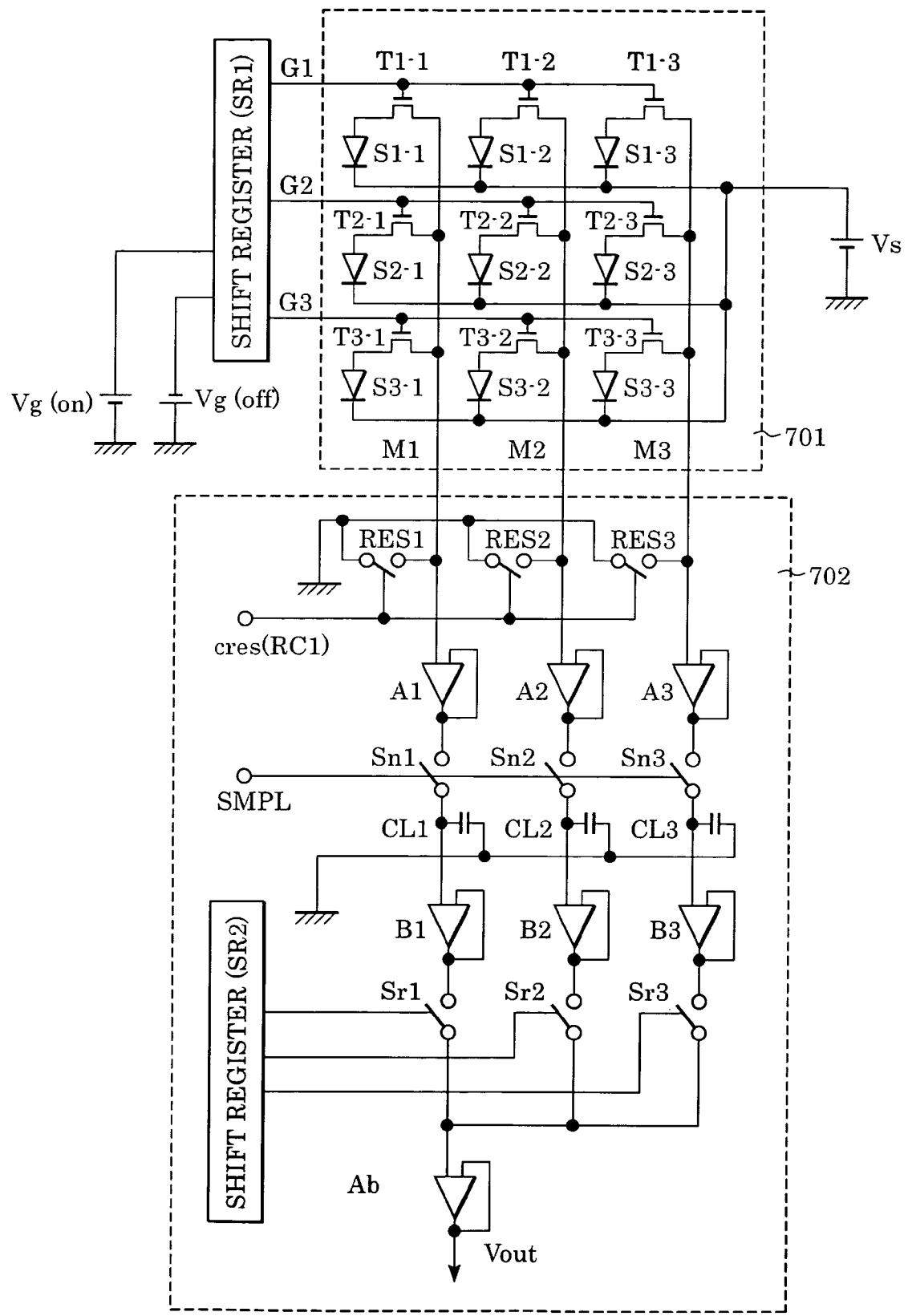
FIG. 8 is a two-dimensional circuit diagram of a photoelectric conversion substrate of the related art including photoelectric conversion elements and switching elements made of amorphous silicon semiconductor thin films.
Figure 9:
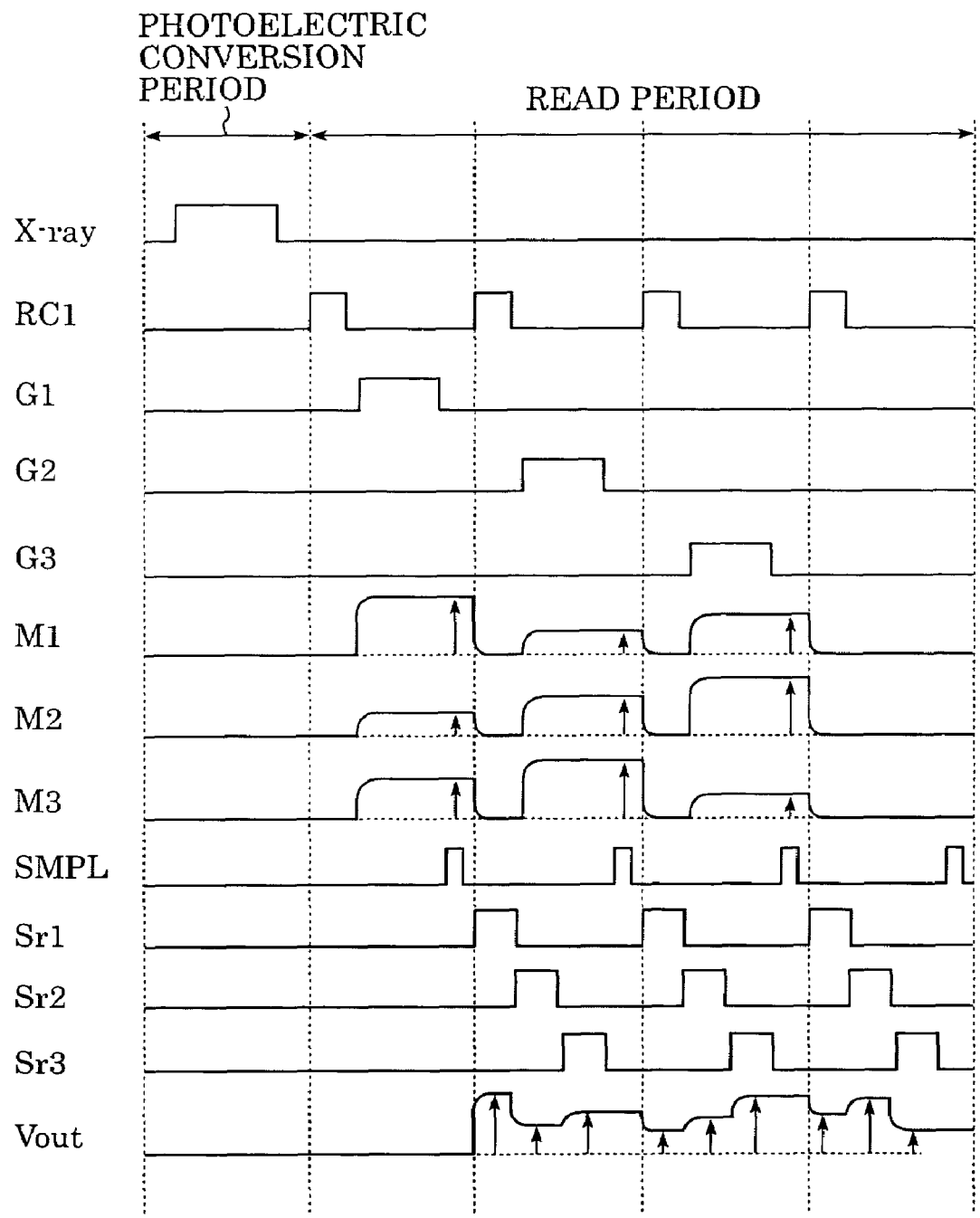
FIG. 9 is a timing chart showing the operation of the photoelectric conversion device of the related art.

In the non-read periods, like the read period in the X-ray imaging apparatus of the related art shown in FIG. 8, signals are sequentially read from the photoelectric conversion elements. However, as described, no charge is accumulated in the photoelectric conversion elements, and the output signal Vout does not change.

In a certain wait period, when the radiographer 1004 presses the irradiation switch 1006 in synchronization with the radiation-induced signal while visually confirming the radiation-induced signal by the radiographer's eye 1008, X-rays are emitted from the X-ray source 1001. The wait period transitions to a photoelectric conversion period, and the photoelectric conversion period follows an actual read period, not a non-read period. The reading operation period is composed of the photoelectric conversion period and the actual read period.

The X-ray irradiation time is determined by an X-ray generator (not shown) including the X-ray source 1001 and the high-voltage power supply 1007. A timing at which the radiographer's hand 1005 releases the irradiation switch 1006 (i.e., a timing at which the irradiation switch 1006 is turned off) does not need to coincide with a timing at which the X-ray irradiation time ends. For example, as shown in FIG. 2, a period of time for which the irradiation switch 1006 is in the on position may be longer than the X-ray irradiation time.

After irradiation of X-rays, transmitted X-ray information of the patient 1002 is obtained in the actual read period. As described above, in the non-read periods, the output signal Vout does not change because X-rays are not emitted in the wait periods prior to the non-read periods. In the actual read period, on the other hand, since X-rays are emitted in the photoelectric conversion period prior to the actual read period and the transmitted X-ray information of the patient 1002 is accumulated in the photoelectric conversion elements of the X-ray imaging apparatus 1003, the accumulated information can be read by a reading operation similar to that in the non-read periods.

In the first embodiment, the idling operation period prior to the reading operation period including the actual read period allows a stable photoelectric converted signal having a stable dark characteristic in proportion to the X-ray dose to be obtained as an output signal.

The radiation-induced signal is generated by the lamp 1009 at a desired timing, and the irradiation switch 1006 is turned on according to the radiation-induced signal, thus allowing radiography without irradiation delay.

Moreover, the radiographer 1004 can turn on the irradiation switch 1006 while perceiving the radiation-induced signal, and therefore electrical connection is not required between the X-ray imaging apparatus 1003 and the X-ray generator via a cable.

Although not shown in FIG. 2, a read operation may be performed without irradiation of X-rays after the reading operation period to obtain dark output offset data. The data in the last non-read period of the idling operation period may be used as dark output offset data.

The frequency at which the radiation-induced signal is generated may be 1 to 4 Hz although it depends upon the reading speed of the X-ray imaging apparatus 1003. If the generation frequency is higher than 4 Hz, the radiation-induced signal is so rapidly pulsed that the radiographer 1004 may not be able to press the irradiation switch 1006 in synchronization with the pulsed radiation-induced signal. If the generation frequency is lower than 1 Hz, the dark component accumulated in the photoelectric conversion elements increases, and the signal-to-noise (S/N) ratio is reduced.

The photoelectric conversion period for which the radiation-induced signal is produced is, for example, several msec to several tens of msec although it depends upon the irradiation time set in the X-ray source 1001. In order to obtain a higher-quality image, the photoelectric conversion period is longer than the irradiation time set in the X-ray source 1001 so that a sufficient amount of transmitted X-ray information can be obtained.

Due to the performance, some radiation imaging apparatuses can reduce the non-read or actual read period for one frame. In these apparatuses, as the operation time for one frame is short, the frequency of the radiation-induced signal increases, and the radiation-induced signal operated according to the timing chart shown in FIG. 2 may not be perceived correctly by the radiographer 1004. In this case, the radiation-induced signal is not produced. For example, one period for every three or four frames so that the radiation-induced signal can be generated at a frequency of 1 to 4 Hz, thus providing desired radiography.

If the timing at which the radiographer 1004 presses the irradiation switch 1006 is delayed, that is, if the irradiation switch 1006 is pressed after a certain time has elapsed since the radiation-induced signal was generated, a desired image may not be obtained. A desired image is not obtained, for example, when the irradiation switch 1006 is operated for a period during which a reading circuit unit reads signals from a photoelectric conversion circuit unit. In order to avoid this problem, for example, a time between generating the radiation-induced signal and pressing the irradiation switch 1006 is monitored, and the operation of the irradiation switch 1006 is not accepted if the monitored time is longer than a predetermined time to prevent irradiation of X-rays. An arrangement for preventing irradiation of X-rays may be an arrangement in which the irradiation switch 1006 does not cause the radiation-induced signal from being generated or in which the X-ray source 1001 does not receive the signal.

In the first embodiment, a still image is obtained in one reading operation period composed of a photoelectric conversion period and an actual read period, by way of example. However, the present invention is not limited to this example, and may be applicable to an embodiment in which a motion picture is obtained by repeating a plurality of reading operation periods.

Second Embodiment

Figure 3:
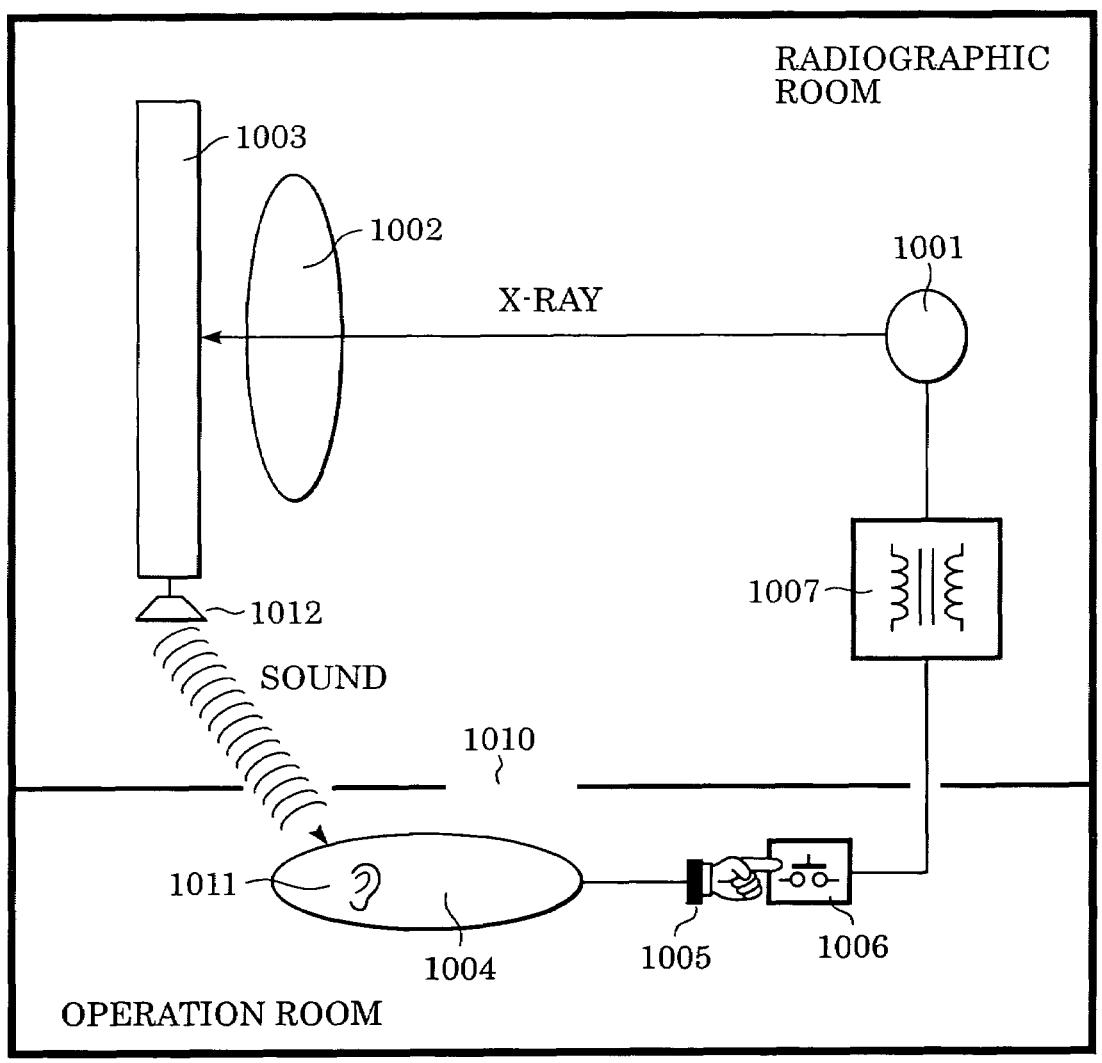
FIG. 3 is a diagram of an X-ray imaging system (radiation imaging system) according to a second embodiment of the present invention.

FIG. 3 illustrates an X-ray imaging system (radiation imaging system) according to a second embodiment of the present invention.

The X-ray imaging system according to the second embodiment includes a loudspeaker 1012, in place of the lamp 1009 in the X-ray imaging system according to the first embodiment, for generating an audio radiation-induced signal instead of an optical signal. The other structure of the X-ray imaging system is similar to that of the first embodiment. For a description of elements 1001, 1007, 1005, 1006, 1002, and 1010 of FIG. 3, see the description of the first embodiment.

The X-ray imaging system according to the second embodiment is also operated according to the timing chart shown in FIG. 2. Specifically, an audio radiation-induced signal is output from the loudspeaker 1012 during the idling operation period of the X-ray imaging apparatus 1003. The radiographer 1004 perceives the audio radiation-induced signal by his/her ear 1011, and turns on the irradiation switch 1006 at a desired radiographic timing. Thus, similar advantages to those of the first embodiment can be achieved.

An optical radiation-induced signal may not be perceived by the radiographer 1004 depending upon the portion to be taken by radiography or the radiographic angle. In the second embodiment, an audio radiation-induced signal can easily be perceived by a radiographer irrespective of the portion to be taken by radiography or the radiographic angle unless particularly high noise occurs.

Third Embodiment

Figure 4:
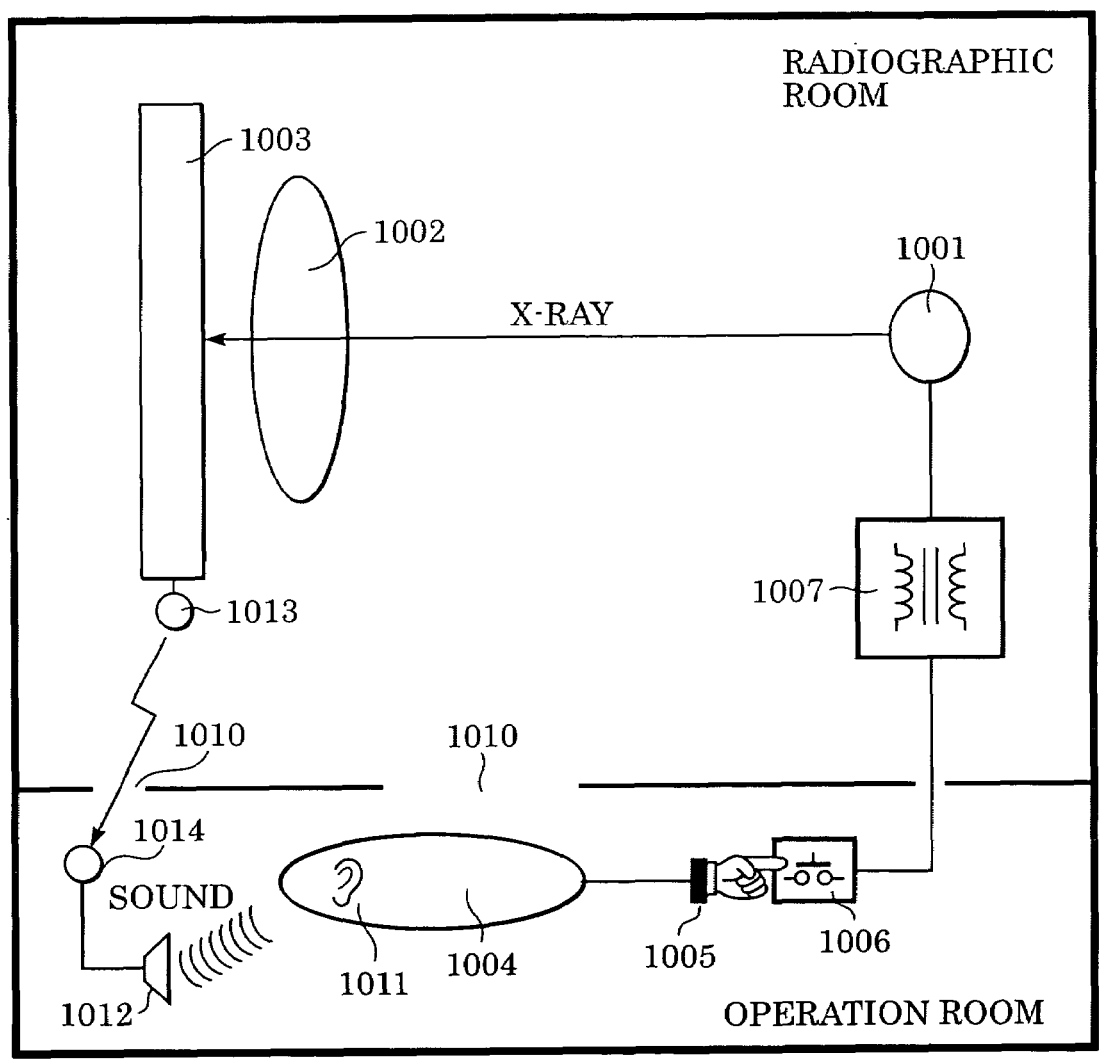
FIG. 4 is a diagram of an X-ray imaging system (radiation imaging system) according to a third embodiment of the present invention.

FIG. 4 illustrates an X-ray imaging system (radiation imaging system) according to a third embodiment of the present invention.

The X-ray imaging system according to the third embodiment includes an infrared LED 1013 for emitting infrared light, in place of the lamp 1009 in the X-ray imaging system according to the first embodiment. In the operation room, the X-ray imaging system according to the third embodiment further includes an infrared sensor 1014 for detecting infrared light emitted from the infrared LED 1013, and a loudspeaker 1012 connected to the infrared sensor 1014. For a description of elements 1001, 1007, and 1010 of FIG. 4, see the description of the first embodiment.

The X-ray imaging system according to the third embodiment is also operated according to the timing chart shown in FIG. 2. Specifically, a radiation-induced signal (infrared light) is emitted from the infrared LED 1013 during the idling operation period of the X-ray imaging apparatus 1003, and the infrared light is immediately detected by the infrared sensor 1014 to output an audio signal from the loudspeaker 1012. The radiographer 1004 perceives the audio radiation-induced signal by his/her ear 1011, and turns on the irradiation switch 1006 with his/her hand 1005 at a desired radiographic timing. Thus, similar advantages to those of the first embodiment can be achieved.

In the second embodiment, the loudspeaker 1012 is located in the radiographic room, and produces a radiation-induced signal in the vicinity of the patient 1002 in the radiographic room, which can place mental pressure on the patient 1002. Moreover, the X-ray shield made of lead or the like between the radiographic room and the operation room can make it difficult for the radiographer 1004 to perceive the audio radiation-induced signal. In the third embodiment, however, sound produced in the operation room can reduce pressure placed on the patient 1002, and can easily be perceived by the radiographer 1004, by placing the loudspeaker 1012 in the operation room.

In the third embodiment, the radiation-induced signal is communicated via wireless communication using the infrared LED 1013 and the infrared sensor 1014. However, the present invention is not limited thereto, and a general signal generator and signal receiver for use in wireless communication may be used.

If the timing at which the radiographer 1004 presses the irradiation switch 1006 is delayed, that is, if the irradiation switch 1006 is pressed after a certain time has elapsed since the radiation-induced signal was generated, a desired image may not be obtained. A desired image is not obtained, for example, when the irradiation switch 1006 is operated for a period during which a reading circuit unit reads signals from a photoelectric conversion circuit unit. In order to avoid this problem, for example, a time period between generating the radiation-induced signal and pressing the irradiation switch 1006 is monitored, and the operation of the irradiation switch 1006 is not accepted if the monitored time is longer than a predetermined time to prevent irradiation of X-rays.

An arrangement for preventing irradiation of X-rays by making the operation of the irradiation switch 1006 unacceptable will now be described with reference to FIG. 10.

FIG. 10 is a timing chart showing an operation for determining whether or not irradiation of X-rays is permitted depending on the timing at which a radiographer turns on an irradiation switch. A monitoring signal (B) is synchronized with a radiation-induced signal (A), and a period of time during which the monitoring signal (B) is high corresponds to a monitoring time. The monitoring time is set in advance in a wait period, except for a non-read period, of the X-ray imaging apparatus. However, the monitoring time is determined not based on the wait period itself but based on a predetermined X-ray irradiation time because it X-rays are emitted, irradiation of X-rays must be stopped until the actual read begins.

The radiographer turns on an irradiation switch (C) according to sound output from the loudspeaker 1012. A delay detection signal (D) is a signal for determining whether or not the irradiation switch (C) is turned on during the monitoring time of the monitoring signal (B). The delay detection signal (D) is the logical AND of the monitoring signal (B) and the irradiation switch (C), i.e., D=B & C. If the delay time of the irradiation switch (C) with respect to the radiation-induced signal (A) is shorter than the monitoring time (B), as shown in FIG. 10, the delay detection signal (D) generates pulses, and X-rays are emitted for a predetermined period of time. If the delay detection signal (D) does not generate pulses, it is determined that the timing at which the irradiation switch is turned on is delayed, and X-rays are not emitted.

In the first or second embodiment, the radiation-induced signal is output as light or sound, and a radiographer directly perceives a monitoring signal using the five senses. In this case, the monitoring signal (B) shown in FIG. 10 is not produced and therefore irradiation of X-rays cannot be stopped. A mechanism for transforming light or sound into a monitoring signal is therefore required.

Fourth Embodiment

Figure 5:
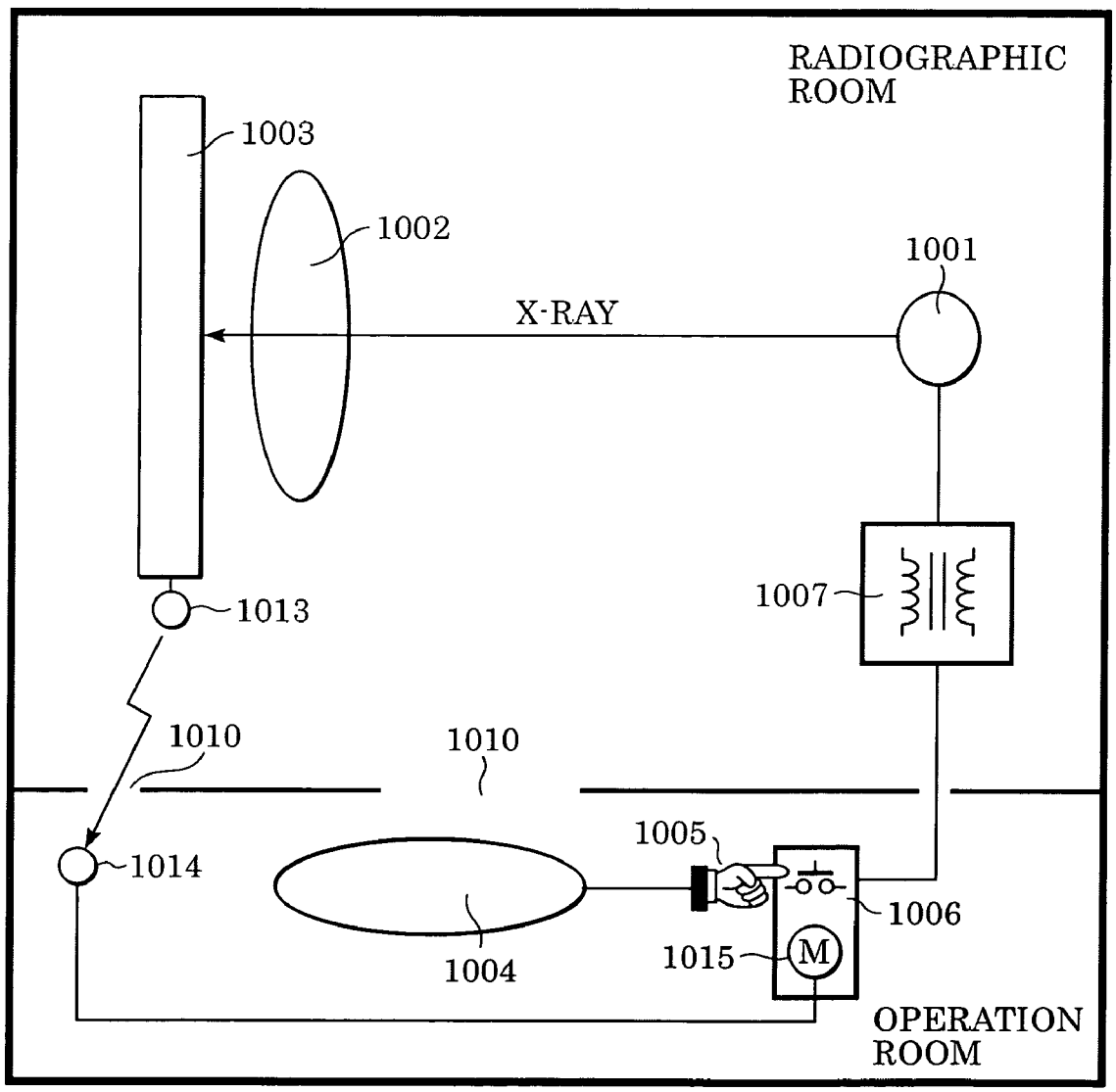
FIG. 5 is a diagram of an X-ray imaging system (radiation imaging system) according to a fourth embodiment of the present invention.

FIG. 5 illustrates an X-ray imaging system (radiation imaging system) according to a fourth embodiment of the present invention.

The X-ray imaging system according to the fourth embodiment includes an infrared LED 1013 for emitting infrared light, in place of the lamp 1009 in the X-ray imaging system according to the first embodiment. In the operation room, the X-ray imaging system according to the fourth embodiment further includes an infrared sensor 1014 for detecting infrared light emitted from the infrared LED 1013, and a motor 1015 connected to the infrared sensor 1014. For example, the motor 1015 is located in the irradiation switch 1006, and serves as a vibration generator.

The X-ray imaging system according to the fourth embodiment is also operated according to the timing chart shown in FIG. 2. Specifically, a radiation-induced signal (infrared light) is emitted from the infrared LED 1013 during the idling operation period of the X-ray imaging apparatus 1003, and the infrared light-is immediately detected by the infrared sensor 1014 to vibrate the irradiation switch 1006 using the motor 1015. The irradiation switch 1006 vibrates when the radiation-induced signal shown in FIG. 2 is high. The radiographer 1004 perceives the vibration of the irradiation switch 1006, i.e., the radiation-induced signal, by the hand 1005, and turns on the irradiation switch 1006 at a desired radiographic timing. Thus, similar advantages to those of the first embodiment can be achieved. For a description of elements 1001, 1002, 1007, and 1010 of FIG. 5, see the description of the first embodiment.

Similarly to the second embodiment, advantageously, the radiographer can easily perceive the radiation-induced signal irrespective of the portion to be taken by radiography or the radiographic angle.

Fifth Embodiment

Figure 6:
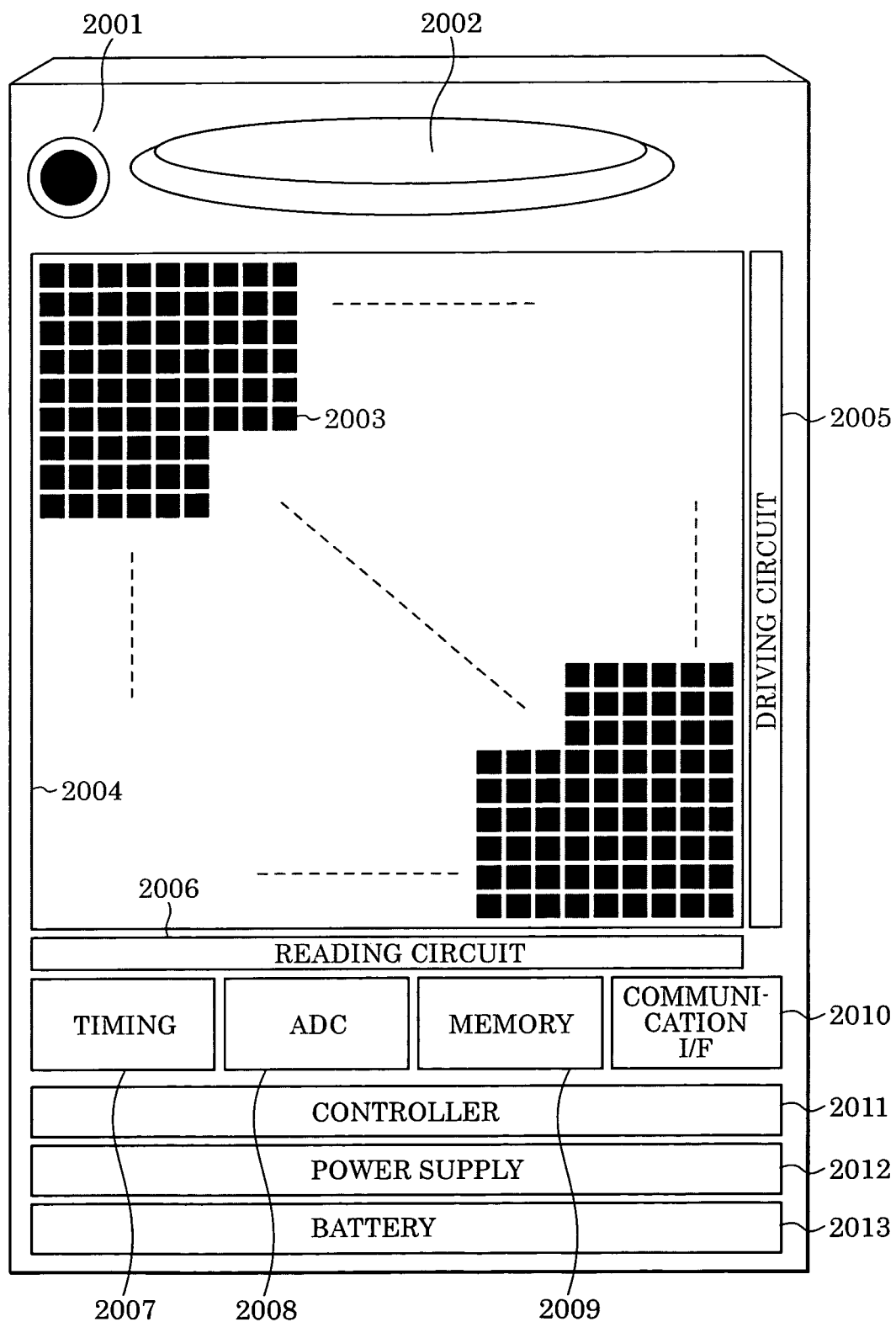
FIG. 6 is a diagram of a radiation imaging apparatus according to a fifth embodiment of the present invention.

FIG. 6 illustrates a cassette-type radiation imaging apparatus according to a fifth embodiment of the present invention.

The cassette-type radiation imaging apparatus according to the fifth embodiment has a thin housing including a loudspeaker 2001, radiation imaging elements 2003, a driving circuit unit 2005, a reading circuit unit 2006, a timing unit 2007, an analog-to-digital converter (ADC) unit 2008, a memory unit 2009, a communication interface (I/F) unit 2010, a controller unit 2011, a power supply unit 2012, and a battery unit 2013.

The loudspeaker 2001 corresponds to the loudspeaker 1012 in the second embodiment, and generates an audio radiation-induced signal. The radiation imaging elements 2003 are arranged as pixels in a two-dimensional array. Although not shown in FIG. 6, each pixel is formed of, for example, a photoelectric conversion element and a switching element. The radiation imaging elements 2003 are arranged in a radiation detection region 2004. For example, the radiation detection region 2004 appears as a frame so that the radiographer can easily identify the region 2004. The driving circuit unit 2005 drives the radiation imaging elements 2003. The reading circuit unit 2006 reads radiation signals from the radiation imaging elements 2003.

The timing unit 2007 outputs a timing signal necessary for obtaining a radiation image to the driving circuit unit 2005 and the reading circuit unit 2006. The ADC unit 2008 converts the analog signals output from the reading circuit unit 2006 into digital signals. The memory unit 2009 stores the digital radiation image data converted by the ADC unit 2008. The communication I/F unit 2010 transmits the digital radiation image data stored in the memory unit 2009 to a hard disk of a personal computer or another recording medium (not shown). The communication I/F unit 2010 further receives, for example, driving conditions for radiography from another medium, and stores the received data into the memory unit 2009.

The controller unit 2011 controls the timing unit 2007, the ADC unit 2008, the memory unit 2009, the communication I/F unit 2010, etc. The power supply unit 2012 supplies necessary power to the timing unit 2007, the ADC unit 2008, the memory unit 2009, the communication I/F unit 2010, the driving circuit unit 2005, the reading circuit unit 2006, etc.

The housing further includes a handle 2002 allowing the radiographer to easily carry the cassette-type radiation imaging apparatus.

The thin housing of the cassette-type radiation imaging apparatus according to the fifth embodiment accommodates the components necessary for radiography, and no cable is therefore required for connecting to an external device during radiography. Therefore, a highly portable, light cordless digital radiation imaging apparatus is feasible. The cassette-type radiation imaging apparatus is easy-to-use and safe even in emergency medical environments in which a patient is radiographed while moving a radiation generator. No cables are required, and the reliability of the apparatus increases.

In the cassette-type radiation imaging apparatus, an indicator for indicating a radiation-induced signal to a radiographer is not limited to the loudspeaker 2001. For example, the cassette-type radiation imaging apparatus may include the lamp 1009 in the first embodiment for emitting visible light, the infrared LED 1013 in the third and fourth embodiments for emitting infrared light, and/or the motor 1015 in the fourth embodiment. The radiation-induced signal indicator may be located in any position other than the position of the loudspeaker 2001 shown in FIG. 6, or a plurality of radiation-induced signal indicators may be provided.

Sixth Embodiment

Figure 7:
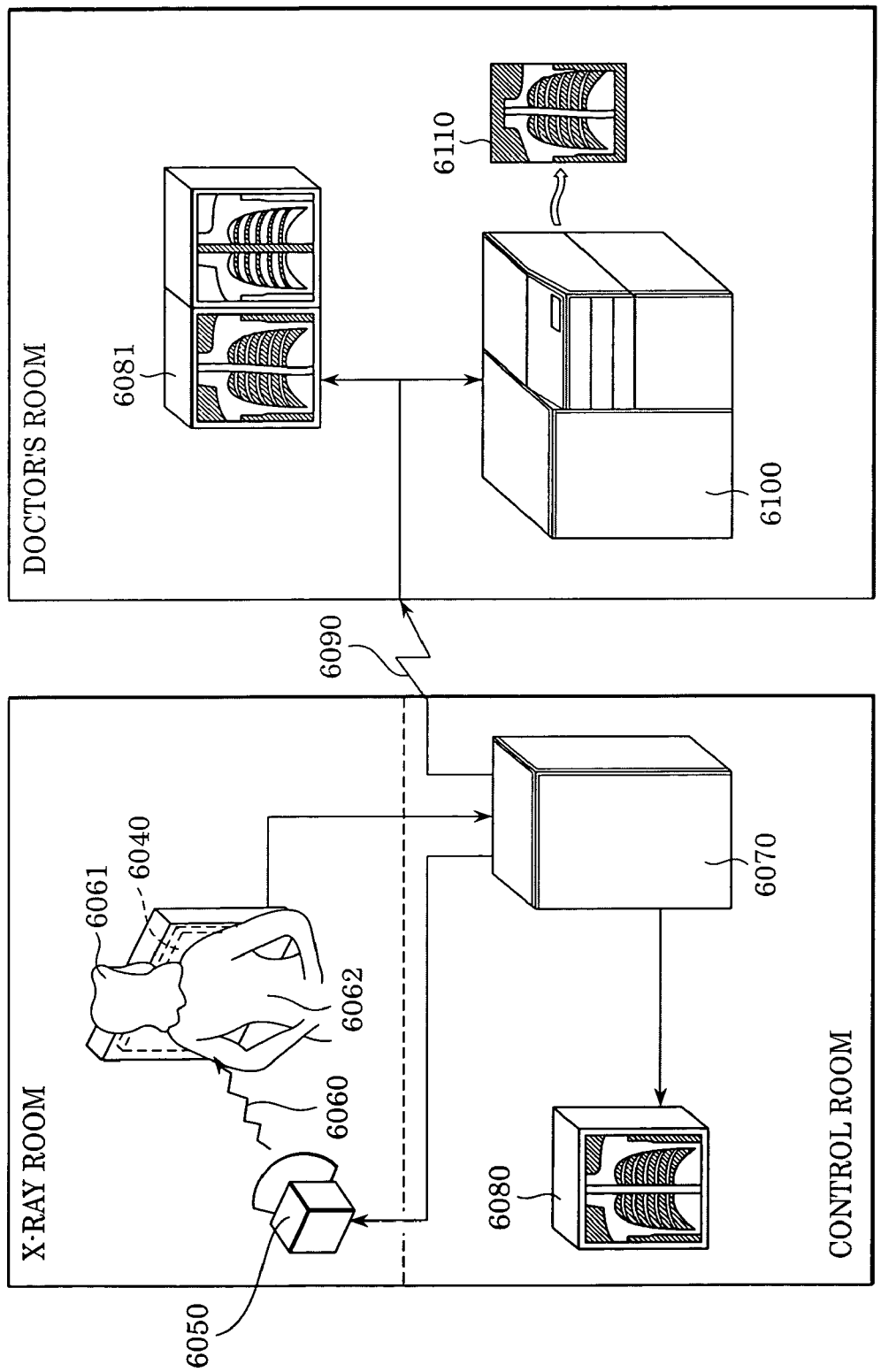
FIG. 7 is a schematic diagram of an X-ray diagnosis system as an application of an X-ray imaging system (radiation imaging system) according to a sixth embodiment of the present invention.

FIG. 7 is a schematic diagram of an X-ray imaging system (radiation imaging system) according to a sixth embodiment of the present invention, which is described in the context of an X-ray diagnosis system.

In an X-ray room (radiographic room), X-rays 6060 emitted from an X-ray tube (X-ray generator) 6050 pass through a chest 6062 of a patient or subject 6061, and enter an image sensor 6040. The X-rays contain body information about the patient 6061. In response to the X-rays incident on the image sensor 6040, a scintillator (phosphor) emits light, and the light is photoelectrically converted by photoelectric conversion elements in a sensor panel to obtain electrical information. The image sensor 6040 outputs the obtained electrical signals (digital signals) to an image processor 6070. The image processor 6070 performs image processing on the received signals, and outputs the resulting signals to a display 6080 in a control room (operation room). A user observes an image displayed on the display 6080 to obtain the body information about the patient 6061. The image processor 6070 also functions as a controller for switching the radiographic mode between a motion-picture mode and a still-image mode and controlling the X-ray tube 6050. The image sensor 6040 includes a radiation-induced signal generator (not shown), e.g., the lamp 1009 in the first embodiment, and the image processor 6070 includes a switch (not shown), e.g., the irradiation switch 1006 in the first embodiment.

The image processor 6070 also transmits the electrical signals output from the image sensor 6040 to a distant place via a transmission medium, such as a telephone line 6090, so as to display them on a display 6081 in another room, e.g., a doctor's room. The electrical signals output from the image sensor 6040 may be stored in a recording medium, such as an optical disc, so that a doctor can conduct diagnose at a distant place using the recording medium. A film processor 6100 may be used for recording onto a film 6110.

The structure of each photoelectric conversion element is not particularly limited in the present invention. For example, a photoelectric conversion element made of amorphous silicon as a main material and capable of absorbing visible light from a wavelength converter that converts radiation into visible light to convert it into electrical signals may be used. For example, a positive-intrinsic-negative (PIN) type photoelectric conversion element including an acceptor-impurity-doped p-layer, an intrinsic semiconductor layer or an i-layer, a donor-impurity-doped n-layer, or an metal insulator semiconductor (MIS) type photoelectric conversion element including a metal thin-film layer formed on a substrate, an amorphous silicon nitride insulating layer formed on the metal thin-film layer for blocking transmission of electrons and holes, a hydrogenated amorphous silicon photoelectric conversion layer formed on the insulating layer, an n-type injection-blocking layer formed on the photoelectric conversion layer for blocking injection of holes, and a conductive layer formed on the injection-blocking layer may be used. In an MIS type photoelectric conversion element, the concoctive layer may be a transparent conductive layer, and the conductive layer may be formed on a portion of the injection-blocking layer. A wavelength converter for use in combination with these photoelectric conversion elements may be made of $Gd_2O_2S$, $Gd_2O_3$, or CsI as a main component. The photoelectric conversion element may contain amorphous selenium, gallium arsenide, lead iodide or mercury iodide, and may absorb radiation and directly convert it into an electrical signal.

The structure of a reading circuit unit is not particularly limited. The reading circuit unit may include, for example, an amplifier for amplifying a signal read from a photoelectric conversion circuit unit, a storage unit for storing the signal amplified by the amplifier, and a serial converter for serially converting the signal stored in the storage unit.

The illustrated embodiments of the present invention may be implemented by, for example, a computer executing a program. A medium for supplying the program to the computer, such as a computer-readable recording medium having the program recorded therein, e.g., a compact disc read-only memory (CD-ROM), or a transmission medium for transmitting the program, e.g., the Internet, may also constitute an embodiment of the present invention. The program may also constitute one embodiment of the present invention. The program, the recording medium, the transmission medium, and the program product fall within the scope of the present invention.

While the present invention has been described with reference to exemplary embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

This application claims priority from Japanese Patent Application No. 2004-106387 filed Mar. 31, 2004, which is hereby incorporated by reference herein.

What is claimed is:

1. A radiation imaging apparatus comprising:
   a conversion circuit unit in which a plurality of pixels including conversion elements are arranged into an array on a substrate;
   a reading circuit unit that reads signals from said conversion circuit unit;
   a controller for controlling said radiation apparatus to take a radiation image in a radiographic operation period, the radiographic operation period comprising an idling operation period alternately including a wait period and a non-read period prior to emission of radiation and a reading operation period subsequent to emission of radiation; and
   a radiation-induced signal generating unit to generate a radiation-induced signal to a radiographer during the idling operation period except for the non-read period for synchronizing the operation of said radiation imaging apparatus with the emission of radiation.

2. A radiation imaging apparatus according to claim 1, wherein said radiation-induced signal generating unit generates a radiation-induced signal for inducing the radiographer to operate a radiation emission switch,
   wherein generation of the radiation-induced signal performed by said radiation-induced signal generating unit and reading of the signals from said conversion circuit unit performed by said reading circuit unit are repeated.

3. A radiation imaging apparatus according to claim 1, wherein the radiation-induced signal comprises at least one selected from a group consisting of visible light, sound, and vibration.

4. A radiation imaging apparatus according to claim 1, wherein the radiation-induced signal has a frequency of 1 to 4 Hz.

5. A radiation imaging apparatus according to claim 1, wherein each pixel of the plurality of pixels includes a switching element connected to each of the conversion elements.

6. A radiation imaging apparatus according to claim 1, further comprising a wavelength converter that converts radiation into visible light,
   wherein each of the conversion elements is made of amorphous silicon, and each of the conversion elements comprises a photoelectric conversion element for absorbing the visible light from a wavelength converter and converting the absorbed light into an electrical signal.

7. A radiation imaging apparatus according to claim 6, wherein each of the photoelectric conversion elements comprises a positive-intrinsic-negative type photoelectric conversion element having an acceptor-impurity-doped p-layer, an 1-layer being an intrinsic semiconductor layer, and a donor-impurity-doped n-layer.

8. A radiation imaging apparatus according to claim 6, wherein each of the photoelectric conversion elements comprises a metal insulator semiconductor type photoelectric conversion element including a metal thin-film layer formed on the substrate, an amorphous silicon nitride insulating layer formed on the metal thin-film layer for blocking transmission of electrons and holes, a hydrogenated amorphous silicon photoelectric conversion layer formed on the insulating layer, an n-type injection-blocking layer formed on the photoelectric conversion layer for blocking injection of the holes, and a conductive layer formed on the injection-blocking layer.

9. A radiation imaging apparatus according to claim 1, wherein the reading circuit unit includes amplifying means for amplifying the signals read from the conversion circuit unit, a storage unit for storing the signals amplified by the amplifying means, and a serial converting unit for serially convening the signals stored in the storage unit.

10. A radiation imaging apparatus according to claim 1, further comprising a wavelength converter that converts a wavelength of the emitted radiation.

11. A radiation imaging apparatus according to claim 10, wherein the wavelength converter is made of one selected from a group consisting of Gd2O2S, Gd2O3, and CsI as a main component.

12. A radiation imaging apparatus according to claim 1, wherein each of the conversion elements contains one compound selected from a group consisting of amorphous selenium, gallium arsenide, lead iodide, and mercury iodide, each conversion element absorbing the emitted radiation and converting the absorbed radiation into an electrical signal.

13. A radiation imaging system comprising:
radiation generator;
a conversion circuit unit in which a plurality of pixels including conversion elements are arranged into an array on a substrate;
a reading circuit unit that reads signals from said conversion circuit unit;
a radiation emission switch for instructing said radiation generator to emit radiation; and
a controller for controlling said radiation imaging system to take a radiation image in a radiographic operation period, the radiographic operation period comprising an idling operation period alternately including a wait period and a non-read period prior to emission of radiation and a reading operation period subsequent to emission of radiation,
wherein said controller controls a radiation-induced signal generating unit to generate a radiation-induced signal to a radiographer during the idling operation period except for the non-read period, the radiographer operating said radiation emission switch at a desired time subsequent to the idling operation period, and
said radiation generator emits radiation when the radiation emission switch is operated.

14. A radiation imaging system according to claim 13, further comprising a radiation-induced signal generating unit for generating a radiation-induced signal for inducing the radiographer to operate said radiation emission switch,
wherein generation of the radiation-induced signal performed by said radiation-induced signal generating unit and reading of the signals from said conversion circuit unit performed by said reading circuit unit are repeated.

15. A method for controlling a radiation imaging apparatus, wherein the radiation imaging apparatus comprises a conversion circuit unit in which a plurality of pixels including conversion elements are arranged into an away on a substrate, a reading circuit unit that reads signals from the conversion circuit unit, and a radiation emission switch for instructing radiation generating means to emit radiation,
said method comprising:
a first step of performing an idling operation alternately including a wait period and a non-read period prior to emission of radiation;
a second step of generating a radiation-induced signal perceivable by a radiographer during the idling operation except for the non-read period; and
a third step of causing the reading circuit unit to read signals accumulated in the conversion circuit unit after the radiation emission switch is operated.

16. A method according to claim 15, wherein the radiation imaging apparatus further comprises a radiation-induced signal generating unit for generating a radiation-induced signal for inducing the radiographer to operate the radiation emission switch, and said second step and said third step are repeatedly performed.

17. A method according to claim 15, wherein when the radiation emission switch is operated for a period of time during which the reading circuit unit reads the signals from the conversion circuit unit, the operation of the radiation emission switch is not accepted.

18. A storage medium storing a program, said program when executed causing a computer to control a radiation imaging apparatus, wherein the radiation imaging apparatus comprises a conversion circuit unit in which a plurality of pixels including conversion elements are arranged into an away on a substrate, a reading circuit unit that reads signals from the conversion circuit unit, and a radiation emission switch for instructing a radiation generator to emit radiation,
said program comprising:
code for causing the radiation imaging apparatus to perform an idling operation alternately including a wait period and a non-read period prior to emission of radiation and to generate a radiation-induced signal perceivable by a radiographer during the idling operation except for the non-read period; and
code for causing the reading circuit unit to read signals accumulated in the conversion circuit unit after the radiation emission switch is operated.

19. A storage medium according to claim 18, wherein the radiation imaging apparatus further comprises a radiation-induced signal generating unit for generating a radiation-induced signal for inducing the radiographer to operate the radiation emission switch, and
generation of the radiation-induced signal performed by the radiation-induced signal generating unit and reading of the signals from the conversion circuit unit performed by the reading circuit unit are repeatedly performed.

20. A radiation imaging system comprising:
radiation generator;
a conversion circuit unit in which a plurality of pixels including conversion elements are arranged into an array on a substrate;
a reading circuit unit that reads signals from said conversion circuit unit; and
a radiation emission switch for instructing said radiation generator to emit radiation;
a controller for controlling said radiation imaging system to take a radiation image in a radiographic operation period, the radiographic operation period comprising an idling operation period alternately including a wait period and a non-read period prior to emission of radiation and a reading operation period subsequent to emission of radiation,
wherein said controller controls a radiation-induced signal generating unit to generate a radiation-induced signal to a radiographer during the idling operation period except for the non-read period so that the radiographer does not operate said radiation emission switch for a period of time unsuitable for radiography and the operation of the radiation emission switch is not accepted when the radiation emission switch is operated for the period of time unsuitable for radiography.

21. A radiation imaging system according to claim 20, wherein a radiation-induced signal is indicated to the radiographer in the wait period during the idling operation period except for the non-read period so that the radiographer does not operate said radiation emission switch for a period of time during which said reading circuit unit reads the signals from said conversion circuit unit.

22. A radiation imaging apparatus according to claim 1, wherein the radiation-induced signal is intermittently produced after the wait period begins.

* * * * *

UNITED STATES PATENT AND TRADEMARK OFFICE
CERTIFICATE OF CORRECTION

PATENT NO. : 7,403,594 B2
APPLICATION NO. : 11/094134
DATED : July 22, 2008
INVENTOR(S) : Tadao Endo et al.

It is certified that error appears in the above-identified patent and that said Letters Patent is hereby corrected as shown below:

ON THE TITLE PAGE [56] REFERENCES CITED:

Foreign Patent Documents, "2002335446 A" should read --2002-335446 A--.

ON THE TITLE PAGE [57] ABSTRACT:

Line 14, "are" should read --is--.

COLUMN 10:

Line 36, "it" should read --if--.

COLUMN 13:

Line 7, "diagnose" should read --diagnosis--.

COLUMN 15:

Line 9, "convening" should read --converting--;
Line 15, "Gd2O2S, Gd2O3," should read --$Gd_2O_2S$, $Gd_2O_3$,--;
Line 24, "radiation" should read --a radiation--; and
Line 60, "away" should read --array--.

UNITED STATES PATENT AND TRADEMARK OFFICE
CERTIFICATE OF CORRECTION

| | | |
|---|---|---|
| PATENT NO. | : 7,403,594 B2 | |
| APPLICATION NO. | : 11/094134 | |
| DATED | : July 22, 2008 | |
| INVENTOR(S) | : Tadao Endo et al. | |

It is certified that error appears in the above-identified patent and that said Letters Patent is hereby corrected as shown below:

COLUMN 16:

Line 47, "radiation" should read --a radiation--.

Signed and Sealed this

Twenty-third Day of December, 2008

JON W. DUDAS
*Director of the United States Patent and Trademark Office*